(12) United States Patent
Ackerson et al.

(10) Patent No.: US 8,986,523 B2
(45) Date of Patent: Mar. 24, 2015

(54) BIOSENSOR CAPACITOR

(75) Inventors: Kristin M. Ackerson, Colchester, VT (US); John J. Ellis-Monaghan, Grand Isle, VT (US); Jeffrey P. Gambino, Westford, VT (US); Yen Li Lim, Essex Junction, VT (US); Polina A. Razina, Amherst, MA (US)

(73) Assignee: International Business Machines Corporation, Armonk, NY (US)

( * ) Notice: Subject to any disclaimer, the term of this patent is extended or adjusted under 35 U.S.C. 154(b) by 533 days.

(21) Appl. No.: 13/353,523

(22) Filed: Jan. 19, 2012

(65) Prior Publication Data

US 2013/0186754 A1    Jul. 25, 2013

(51) Int. Cl.

| | |
|---|---|
| *G01N 27/327* | (2006.01) |
| *G01R 27/26* | (2006.01) |
| *G01N 27/22* | (2006.01) |
| *H01L 23/00* | (2006.01) |
| *H01L 23/522* | (2006.01) |

(52) U.S. Cl.
CPC .......... *G01N 27/3276* (2013.01); *G01N 27/22* (2013.01); *H01L 23/5223* (2013.01); *H01L 24/05* (2013.01); *H01L 24/13* (2013.01); *H01L 2224/4847* (2013.01); *H01L 24/45* (2013.01); *H01L 2224/45144* (2013.01); *H01L 2224/45147* (2013.01); *H01L 24/03* (2013.01); *H01L 24/48* (2013.01); *H01L 2224/036* (2013.01); *H01L 2224/05157* (2013.01); *H01L 2224/0518* (2013.01); *H01L 2224/05181* (2013.01); *H01L 2224/05184* (2013.01); *H01L 2224/05186* (2013.01); *H01L 2224/05624* (2013.01); *H01L 2224/13101* (2013.01); *H01L 2924/1306* (2013.01)
USPC .................... 204/403.01; 324/649; 422/82.01

(58) Field of Classification Search
CPC . G01N 27/22; G01N 27/227; G01N 27/3272; G01N 2027/22
See application file for complete search history.

(56) References Cited

U.S. PATENT DOCUMENTS

| | | | | |
|---|---|---|---|---|
| 5,605,662 | A | * | 2/1997 | Heller et al. ................. 422/68.1 |
| 5,632,957 | A | | 5/1997 | Heller et al. |
| 6,236,096 | B1 | | 5/2001 | Chang et al. |
| 6,682,936 | B2 | | 1/2004 | Kovacs |
| 6,740,214 | B1 | * | 5/2004 | Dobson et al. ............. 204/403.1 |
| 7,413,859 | B2 | | 8/2008 | Paulus et al. |
| 7,575,720 | B2 | | 8/2009 | Novak et al. |

(Continued)

FOREIGN PATENT DOCUMENTS

EP        1452867 B1    6/2006

OTHER PUBLICATIONS

Balasubramanian et al., Si-Based Sensor for Virus Detection, IEEE Sensors Journal, vol. 5, No. 3, Jun. 2005, pp. 340-344.

(Continued)

*Primary Examiner* — Alexander Noguerola
(74) *Attorney, Agent, or Firm* — Michael J. LeStrange; Hoffman Warnick LLC

(57) ABSTRACT

A biosensor capacitor, including a dielectric layer; a first metal layer in the dielectric layer; a passivation layer over the dielectric layer and the first metal layer; an isolation layer over the passivation layer; a probe DNA electrode connected to the first metal layer; a counter electrode connected to the first metal layer wherein the counter electrode forms an enclosure around the probe DNA electrode; and a bond pad connected to the first metal layer.

18 Claims, 24 Drawing Sheets

(56) References Cited

U.S. PATENT DOCUMENTS

| | | | |
|---|---|---|---|
| 7,670,557 | B2 | 3/2010 | Frey et al. |
| 7,943,394 | B2 | 5/2011 | Flandre et al. |
| 2004/0023253 | A1 | 2/2004 | Kunwar et al. |
| 2006/0105449 | A1* | 5/2006 | Larmer et al. ............ 435/287.2 |
| 2006/0226030 | A1 | 10/2006 | Hanke et al. |
| 2007/0236224 | A1 | 10/2007 | Augustyniak et al. |
| 2010/0052080 | A1* | 3/2010 | Garcia Tello et al. ........ 257/414 |
| 2010/0122904 | A1 | 5/2010 | Hassibi et al. |
| 2010/0221846 | A1 | 9/2010 | Widdershoven |
| 2010/0300899 | A1 | 12/2010 | Levine et al. |
| 2011/0155586 | A1 | 6/2011 | Elibol et al. |

OTHER PUBLICATIONS

Stagni et al., A Fully Electronic Label-Free DNA Sensor Chip, IEEE Sensors Journal, vol. 7, No. 4, Apr. 2007, pp. 577-585.

Estrela et al., Electrical detection of biomolecular interacions with metal-insulator-semiconductor diodes, Biosensors and Bioelectronics 20, 2005, pp. 1580-1586.

Hofmann et al., Fully Electronic DNA Detection on a CMOS Chip: Device and Process Issues, IEEE, Copyright 2002, pp. 488-491.

Wang et al., A novel dual mode capacitor biosensor for real-time, label-free DNA detection, Undated, 4 pages, To the Exmainer's best knowledge published in Electron Devices Meeting, 2006. IEDM '06 International, publisher IEEE.

Thewes et al., A CMOS Medium Density DNA Microarray with Electronic Readout, Mater. Res. Soc. Symp. Proc., vol. 869, Copyright 2005 Materials Research Society, 11 pages.

Guiducci et al., Microelectrodes on a Silicon Chip for Label-Free Capacitive DNA Sensing, IEEE Sensors Journal, vol. 6, No. 5, Oct. 2006, pp. 1084-1093.

* cited by examiner

BIOSENSOR CAPACITOR

BACKGROUND OF THE INVENTION

The present invention relates generally to biosensor capacitors. In particular, the present invention provides a biosensor capacitor connected to a bond pad.

Referring to FIG. 1 and FIG. 2, a cross-section view (FIG. 1) and a top down view (FIG. 2) of a known biosensor capacitor 10 are shown. Known biosensor capacitor 10 includes an oxide layer 12 over a silicon layer 14. An opening in the oxide layer 12 includes a gold layer 16 at the bottom of the opening. A gold counter electrode 18 surrounds the opening at the top of the oxide layer 12. A photoresist layer 20 surrounds the gold counter electrode 18.

Deoxyribonucleic acid (DNA) sensing may be performed using known biosensor capacitor 10 to detect the presence of certain types of biological substances in a sample. Probe (also known as "receptor") DNA is placed on the gold layer 16. An electrolyte sample 22 is placed over the gold layer 16 and the probe DNA. The probe DNA is negatively charged. An applied positive charge to the gold layer 16 will attract the probe DNA. If the electrolyte sample includes a target DNA, the target DNA will hybridize with the probe DNA. The physical characteristics of the hybridized DNA may be detected using a measuring device 24, for example, fluorescence detectors, capacitors, field effect transistors, magnetic sensors, or the like.

BRIEF SUMMARY OF EMBODIMENTS OF THE INVENTION

A first aspect of the invention includes a biosensor capacitor, comprising: a dielectric layer; a first metal layer in the dielectric layer; a passivation layer over the dielectric layer and the first metal layer; an isolation layer over the passivation layer; a probe DNA electrode connected to the first metal layer; a counter electrode connected to the first metal layer wherein the counter electrode forms an enclosure around the probe DNA electrode; and a bond pad connected to the first metal layer.

A second aspect of the invention includes a method, comprising: forming a bond pad via, a counter electrode via, and a probe DNA electrode via through an isolation layer and a passivation layer to a first metal layer in a dielectric layer; forming a first diffusion barrier in each via over the first metal layer; forming a probe DNA electrode by forming a second metal layer over the first diffusion barrier in the probe DNA electrode via; forming a counter electrode in counter electrode via, wherein the counter electrode forms an enclosure around the probe DNA electrode via; and forming a bond pad in one of the bond pad via.

A third aspect of the invention includes a biosensor capacitor, comprising: a dielectric layer; a first metal layer in the dielectric layer; a passivation layer over the dielectric layer and the first metal layer; an isolation layer over the passivation layer; a probe DNA electrode including copper connected to the first metal layer; a counter electrode including copper connected to the first metal layer; and a bond pad including copper connected to the first metal layer.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF EMBODIMENTS OF THE INVENTION

Figure 1:
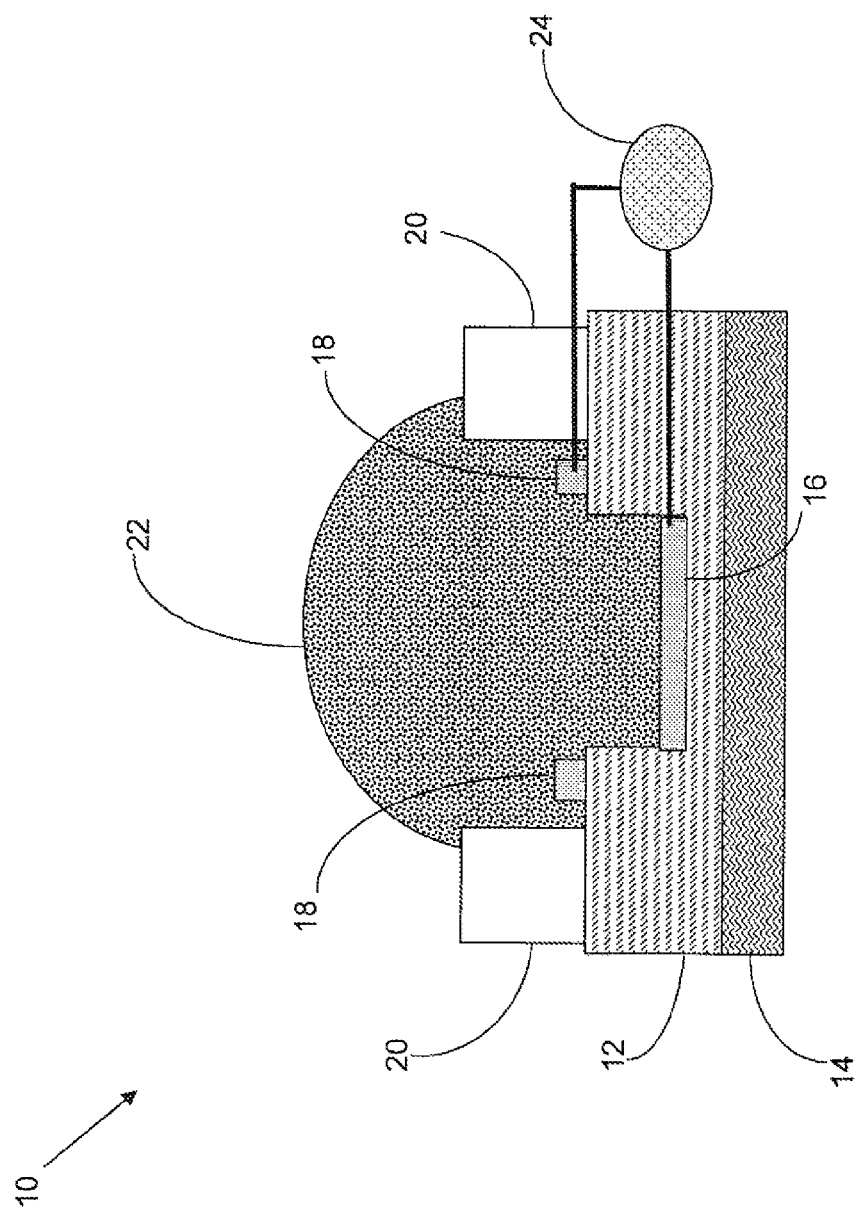
FIG. 1 shows a cross-section view of a known biosensor capacitor.
Figure 2:
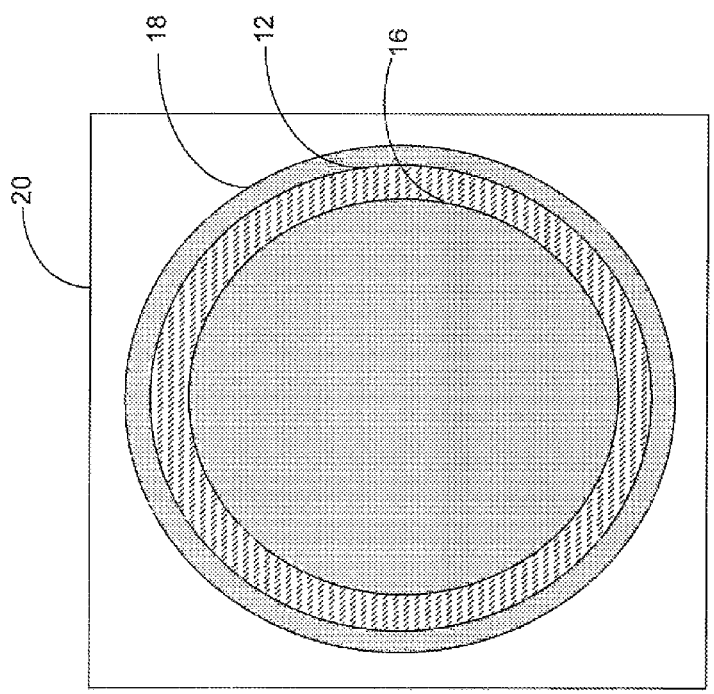
FIG. 2 shows a top down view of a known biosensor capacitor.
Figure 3:
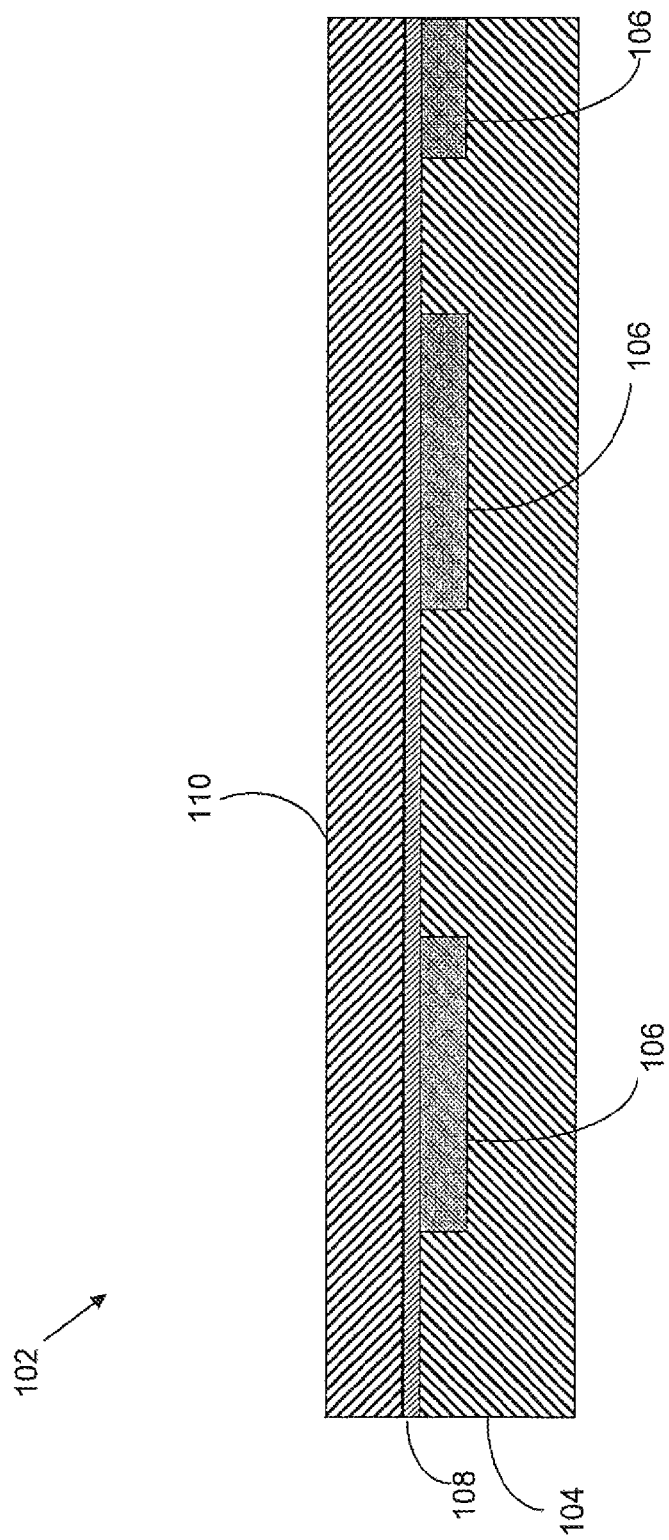
FIGS. 3-24 show various processes in the forming of a biosensor capacitor in accordance with embodiments of this invention.

Referring to FIG. 3, a cross-section view of one embodiment of a process in the forming of a biosensor capacitor 102 in accordance with this invention is shown. Biosensor capacitor 102 includes a dielectric layer 104. A first metal layer 106 may be formed in the dielectric layer 104 using conventional interconnect processes. First metal layer 106 can be used to form wiring from the biosensor capacitor 102 to additional devices built in the semiconductor substrate (not shown), such as CMOS devices (see FIG. 24). First metal layer 106 may include copper ("Cu"), aluminum ("Al"), silver ("Au"), gold ("Au"), or any other suitable metal or alloys (e.g. AlCu, AlCuSi, CuMn, CuAg, CuAl). A passivation layer 108 may be deposited over the dielectric layer 104 and first metal layer 106. Passivation layer 108 may passivate surfaces of the biosensor capacitor 102. Passivation layer 108 may include, for example, silicon nitride and silicon carbon nitride. An isolation layer 110 may be deposited over the passivation layer 108. Isolation layer 110 may provide isolation between first metal layer 106 and subsequent features to be described herein. Isolation layer 110 may include, for example, silicon dioxide, hydrogenated silicon oxycarbide (SiCOH), and polyimide.

Dielectric layer 104 may include, for example, silicon oxide ($SiO_2$), silicon nitride (SiN), or any other suitable material. Any number of dielectric layers may be included in biosensor capacitor 102, as may other layers included in semiconductor chips now known or later developed. In one embodiment, dielectric layer 104 may include silicon oxide ($SiO_2$) for its insulating, mechanical and optical qualities. Dielectric layer 104 may also be formed using silicon nitride ($Si_3N_4$), fluorinated $SiO_2$ (FSG), hydrogenated silicon oxycarbide (SiCOH), porous SiCOH, boro-phospho-silicate glass (BPSG), silsesquioxanes, carbon (C) doped oxides (i.e., organosilicates) that include atoms of silicon (Si), carbon (C), oxygen (O), and/or hydrogen (H), thermosetting polyarylene ethers, SiLK (a polyarylene ether available from Dow Chemical Corporation), a spin-on silicon-carbon containing polymer material available form JSR Corporation, other low dielectric constant (<3.9) material, or layers thereof. Dielectric layer 104 may be deposited using conventional techniques described herein and/or those known in the art.

As used herein, the term "depositing" may include any now known or later developed techniques appropriate for the material to be deposited including but are not limited to, for example: chemical vapor deposition (CVD), low-pressure CVD (LPCVD), plasma-enhanced CVD (PECVD), semi-atmosphere CVD (SACVD) and high density plasma CVD (HDPCVD), rapid thermal CVD (RTCVD), ultra-high vacuum CVD (UHVCVD), limited reaction processing CVD (LRPCVD), metalorganic CVD (MOCVD), sputtering deposition, ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating, and evaporation.

Figure 4:
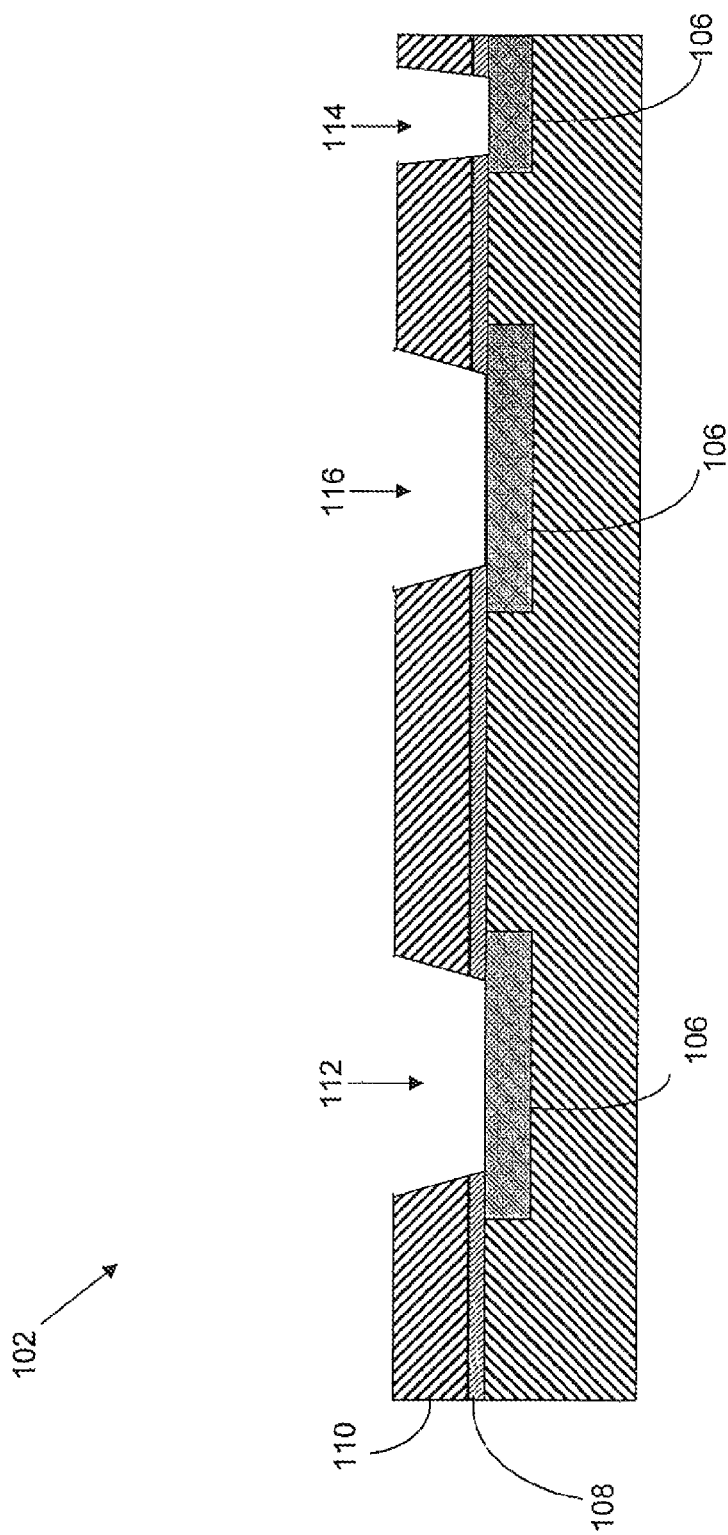

Referring to FIG. 4, a cross-section view of one embodiment of another process in the forming of biosensor capacitor 102 in accordance with this invention is shown. FIG. 4 shows etching through the isolation layer 110 and the passivation layer 108 and exposing the first metal layer 106 and forming a bond pad via 112, a counter electrode via 114, and a probe DNA electrode via 116. Etching may include, for example, photolithography or reactive ionization.

Figure 5:
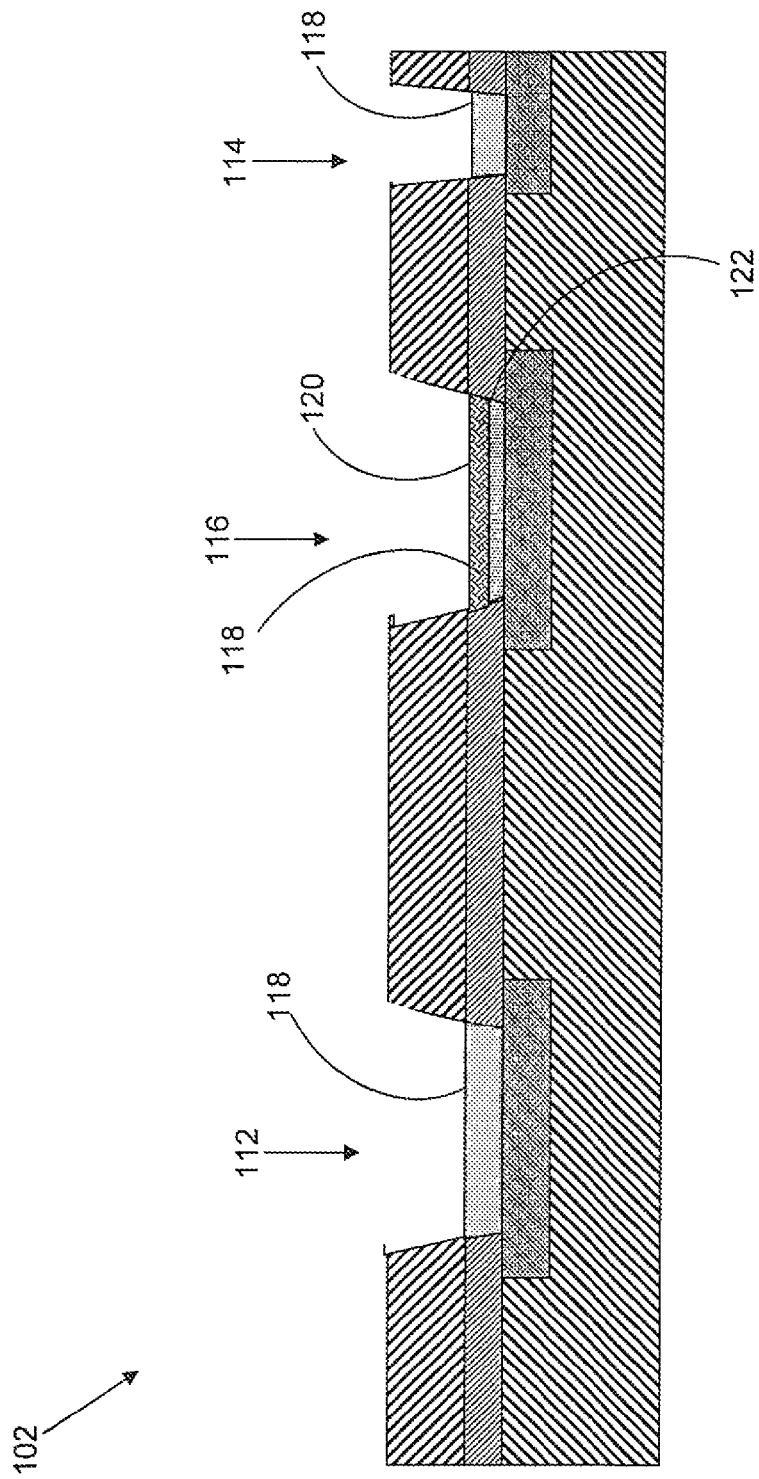

Referring to FIG. 5, a cross-section view of one embodiment of another process in the forming of biosensor capacitor 102 in accordance with this invention is shown. FIG. 5 shows depositing a first diffusion barrier 118 in the bond pad via 112, the counter electrode via 114, and the probe DNA electrode via 116 and over the first metal layer 106. First diffusion barrier 118 may include, for example, a refractory metal including cobalt tungsten phosphide ("CoWP"), tantalum ("Ta"), tantalum nitride ("TaN"), tungsten ("W"), and molybdenum ("Mo") and alloys of the refractory metal. A second metal layer 120 may be selectively deposited in the probe DNA electrode via 116 over the first diffusion barrier 118 forming a probe DNA electrode 122. Second metal layer 120 may include, for example, gold ("Au"), platinum ("Pt"), palladium ("Pd"), nickel ("Ni"), and chromium ("Cr") and alloys, for example, platinum palladium ("PtPd") and nickel chromium ("NiCr"). First diffusion barrier 118 may prevent reactions between the second metal layer 120 and the first metal layer 106.

Figure 6:
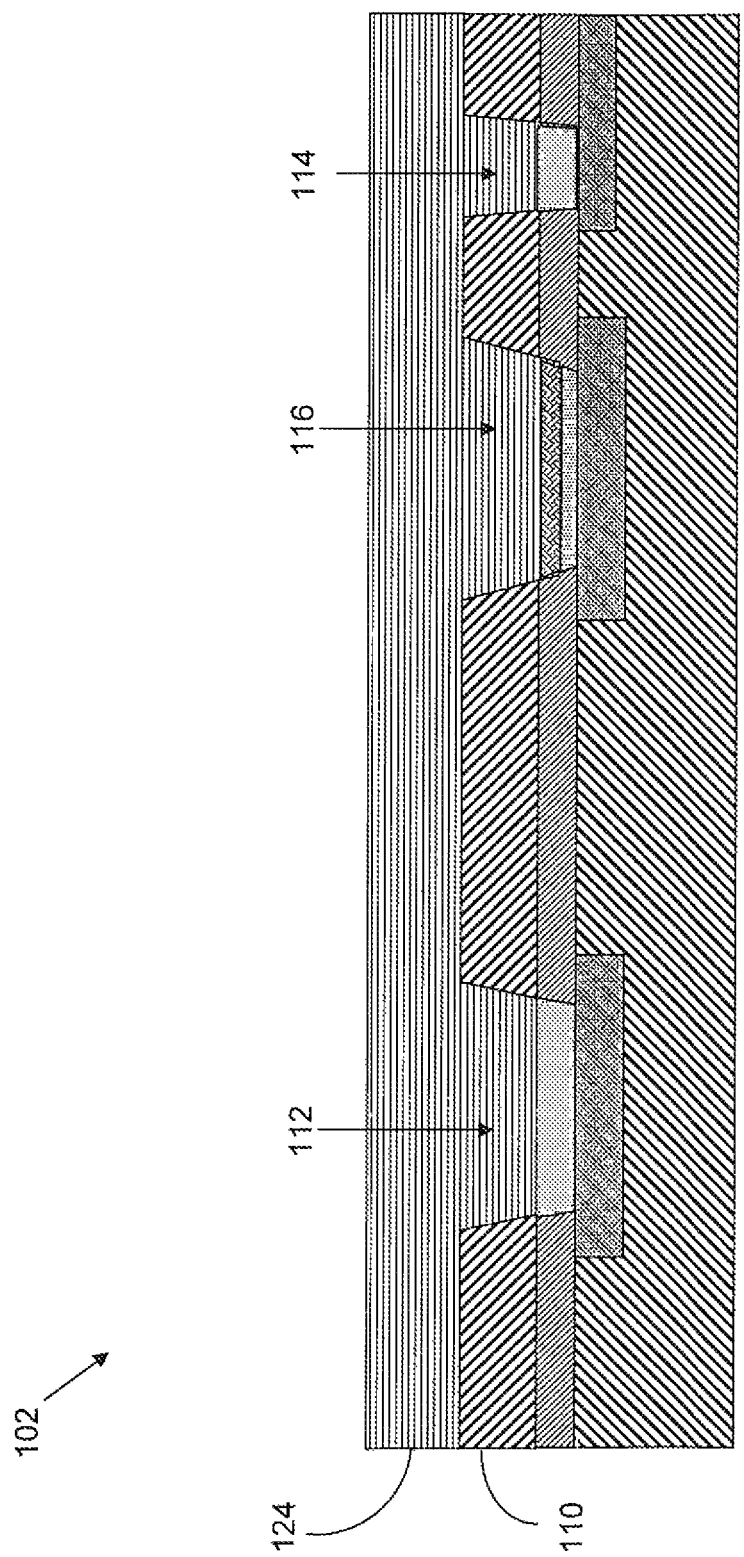
Figure 7:
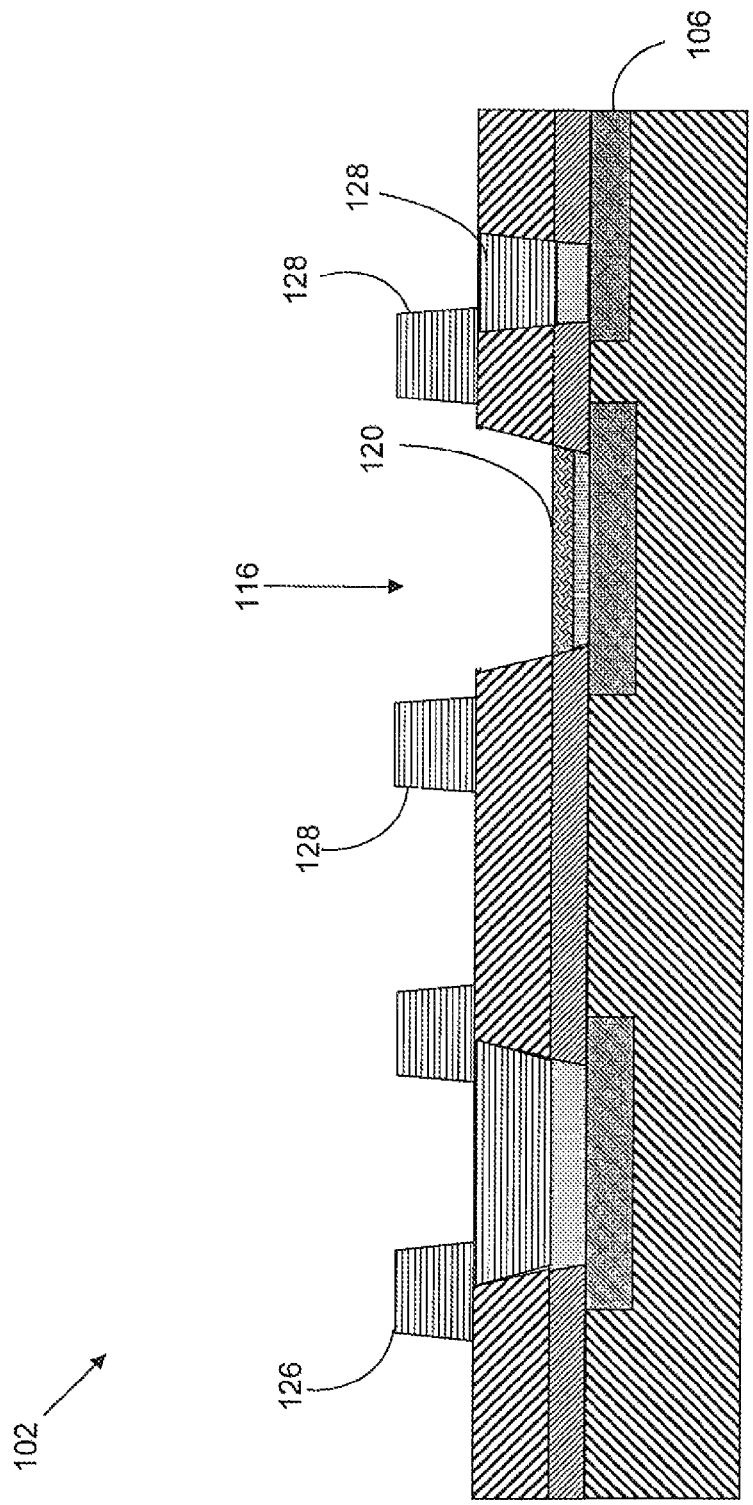

Referring to FIGS. 6 and 7, a cross-section view of one embodiment of other steps in the forming of biosensor capacitor 102 in accordance with this invention is shown. FIG. 6 shows depositing an aluminum layer 124 filling the bond pad via 112, the counter electrode via 114, and the probe DNA electrode via 116 and over the isolation layer 110. FIG. 7 shows etching the aluminum layer 124. Etching the aluminum layer 124 may expose the second metal layer 120. Etching the aluminum layer 124 may complete a bond pad 126. Etching the aluminum layer 124 may form a counter electrode 128 substantially enclosing the probe DNA electrode via 116. Counter electrode 128 may connect with first metal layer 106. Using aluminum layer 124 for bond pad 126 may be preferred for a wirebonding attachment or a solder ball attachment. A person skilled in the art will recognize that other metals may be used, for example, nickel, copper, and the like. Using aluminum layer 124 for forming counter electrode 128 may reduce the processes required to form biosensor capacitor 102.

Figure 8:
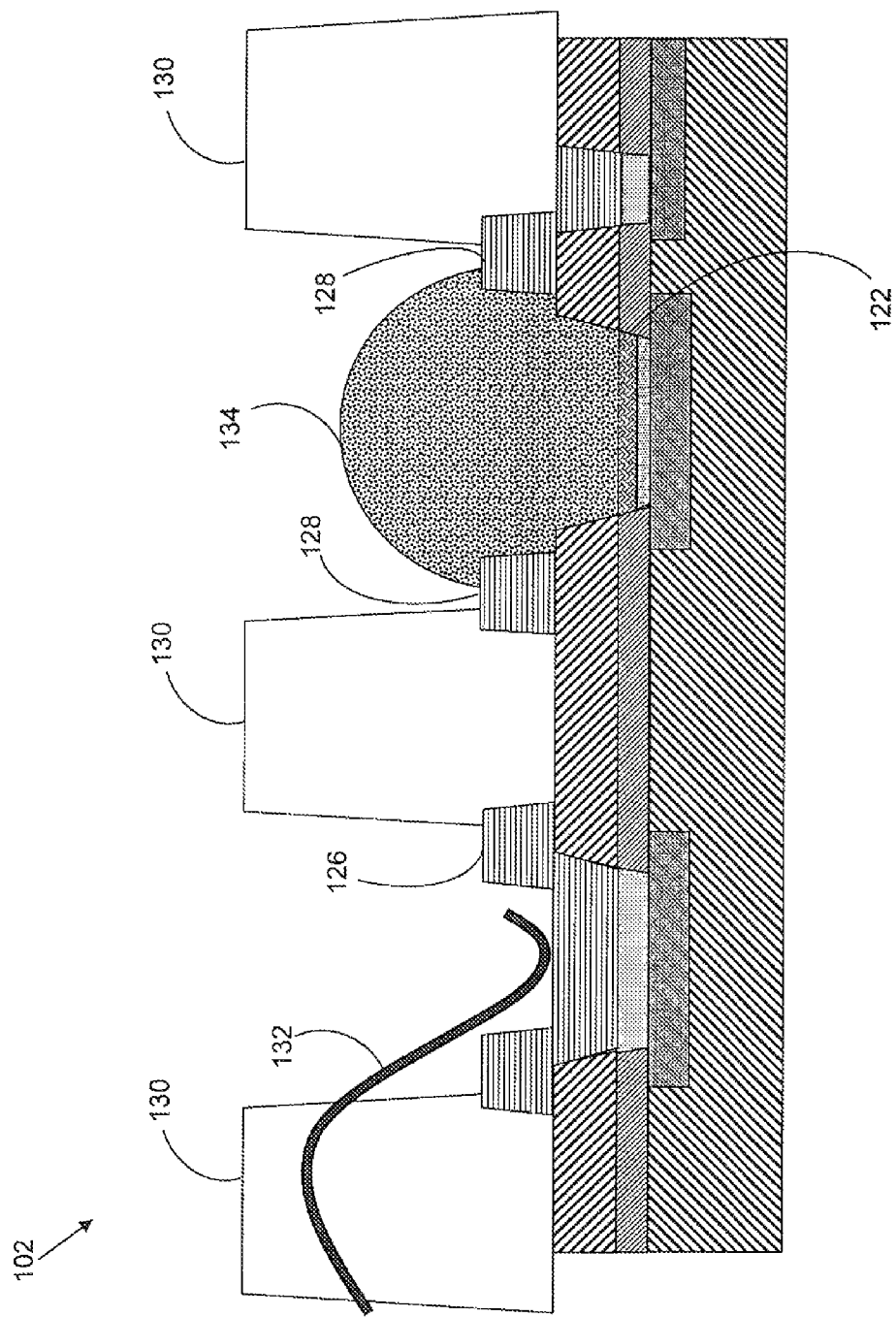
Figure 24:
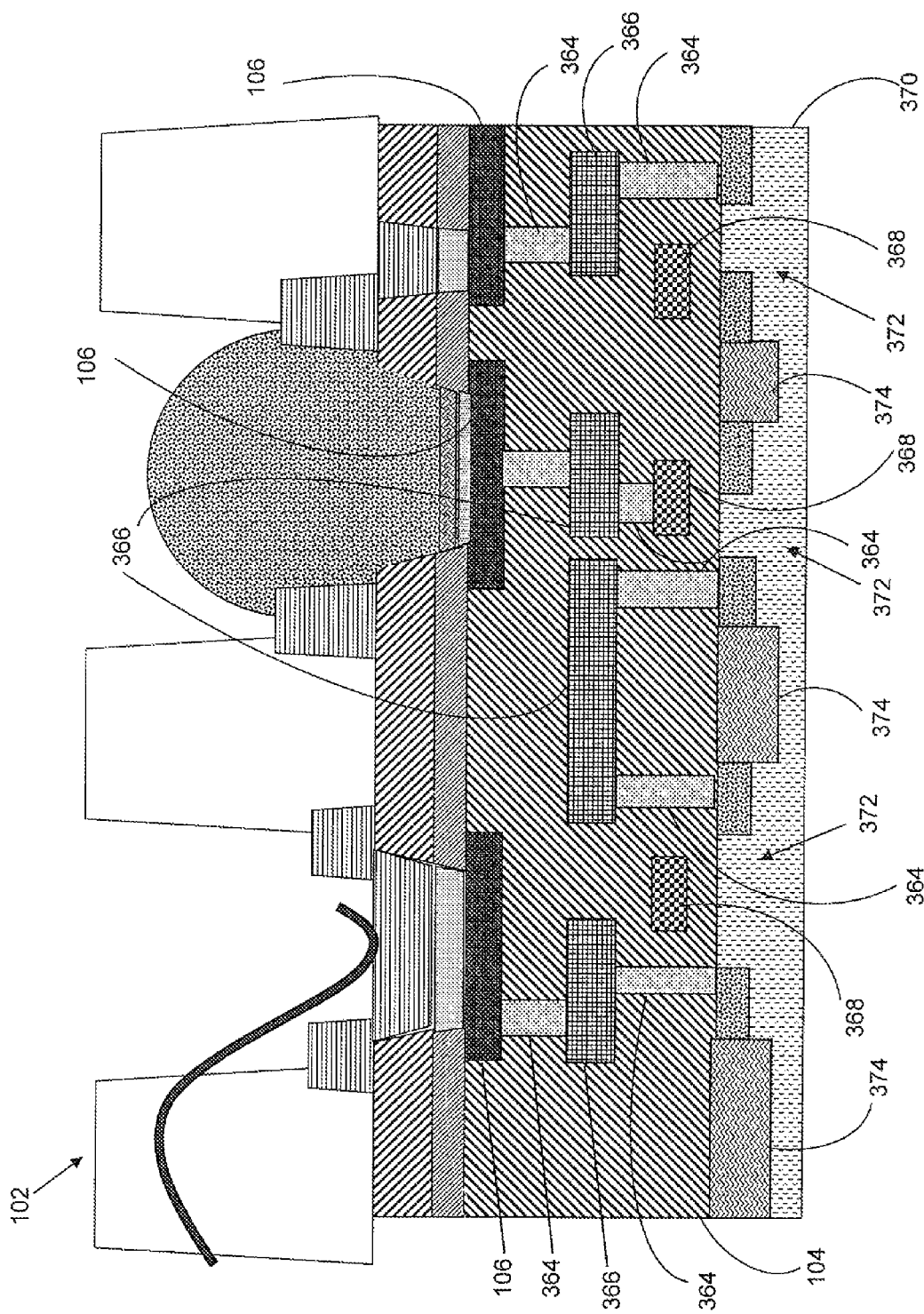

Referring to FIG. 8, a cross-section view of one embodiment of another process in the forming of biosensor capacitor 102 in accordance with this invention is shown. A protective layer 130 may be deposited and patterned to expose the bond pad 126, the counter electrode 128 and the probe DNA electrode 122. Protective layer 130 may protect surfaces of biosensor capacitor 102 from mechanical damage. Protective layer 130 may include, for example, polyimide and other suitable polymer dielectrics. A wire bond 132 or solder ball (not shown) connection may be formed in the protective layer 130 and connected with bond pad 126 using any now known or to be developed method. Wire bond 132 may include, for example, Au or Cu. Electrolyte sample 134 is shown deployed above probe DNA electrode 122 and inside counter electrode 128. An example of biosensor capacitor 102 connected with a field effect transistor device 362 is shown in FIG. 24.

Figure 9:
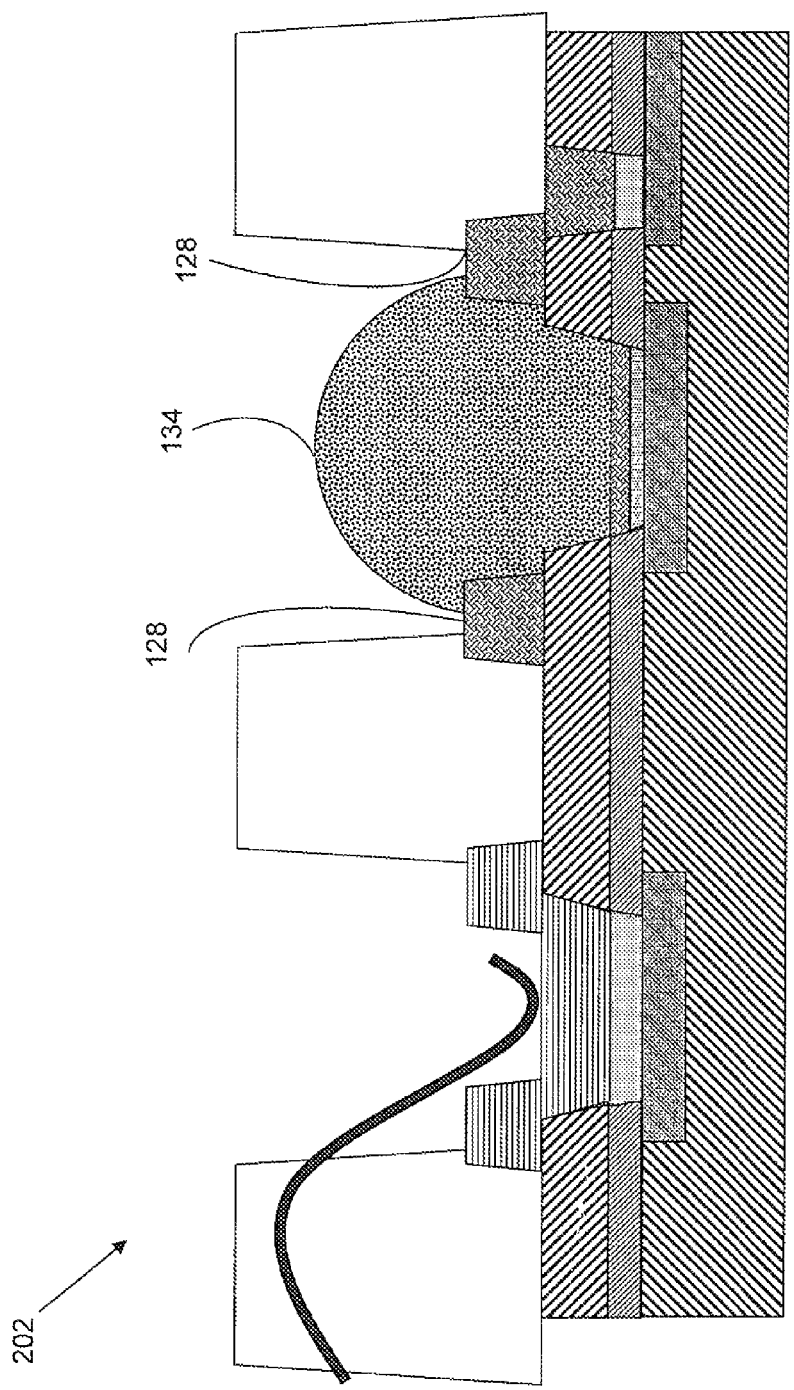

Referring to FIG. 9, a cross-section view of one alternative embodiment of another process in the forming of a biosensor capacitor 202 in accordance with this invention is shown. Biosensor capacitor 202 is substantially similar to biosensor capacitor 102 (FIG. 8) with the exception that the counter electrode 128 may include Au and the bond pad 126 includes Al. A person skilled in the art will readily recognize that additional patterning, deposition and etching processes after the process shown in FIG. 7 may be used to form the counter electrode 128 including Au. All other processes in forming biosensor capacitor 202 are substantially similar to the processes described in forming biosensor capacitor 102. Electrolyte sample 134 is shown deployed above probe DNA electrode 122 and inside counter electrode 128. Using aluminum layer 124 may be preferred for bond pad 126. Using Au for forming counter electrode 128 may provide corrosion resistance when counter electrode 128 is in exposed to electrolyte sample 134.

Figure 10:
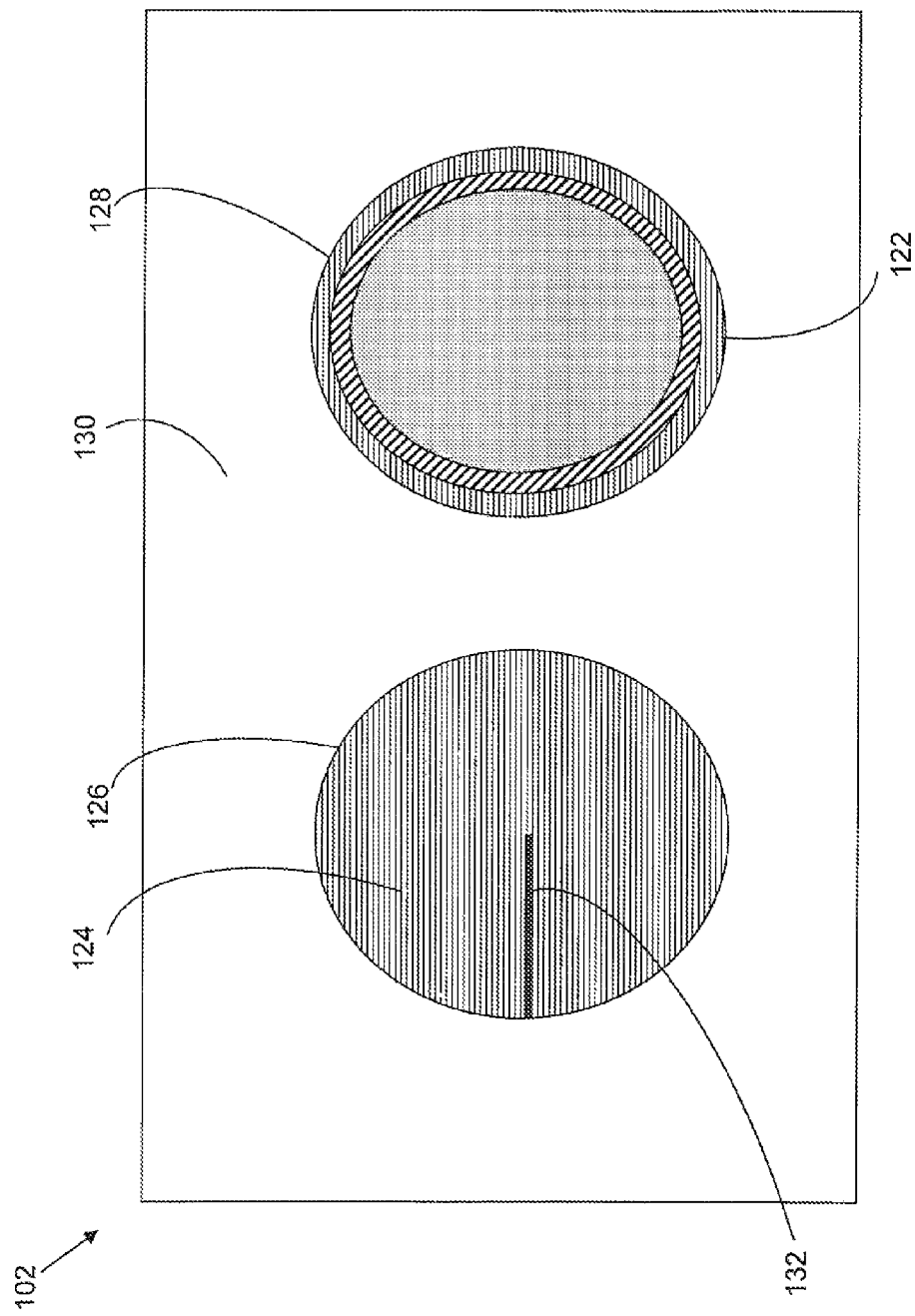

Referring to FIG. 10, a top down view of biosensor capacitor 102 (and similarly biosensor capacitor 202) as shown in FIG. 8 (and similarly FIG. 9) in accordance with this invention is shown. Counter electrode 128 forms an enclosure around probe DNA electrode 122. The enclosure is shown as circular but may take any shape including, for example, oval, rectangular, square, or the like. Bond pad 126 may include the aluminum layer 124. Counter electrode 128, probe DNA electrode 122, and bond pad 126 may be surrounded by protective layer 130. Wire bond 132 or solder ball (not shown) may connect with bond pad 126. Counter electrode 128, probe DNA electrode 122, and bond pad 126 are shown substantially circular in shape. A person skilled in the art will readily recognize that counter electrode 128, probe DNA electrode 122, and bond pad 126 may comprise other enclosure-type shapes to hold electrolyte sample 134 (FIGS. 8 and 9)

Figure 11:
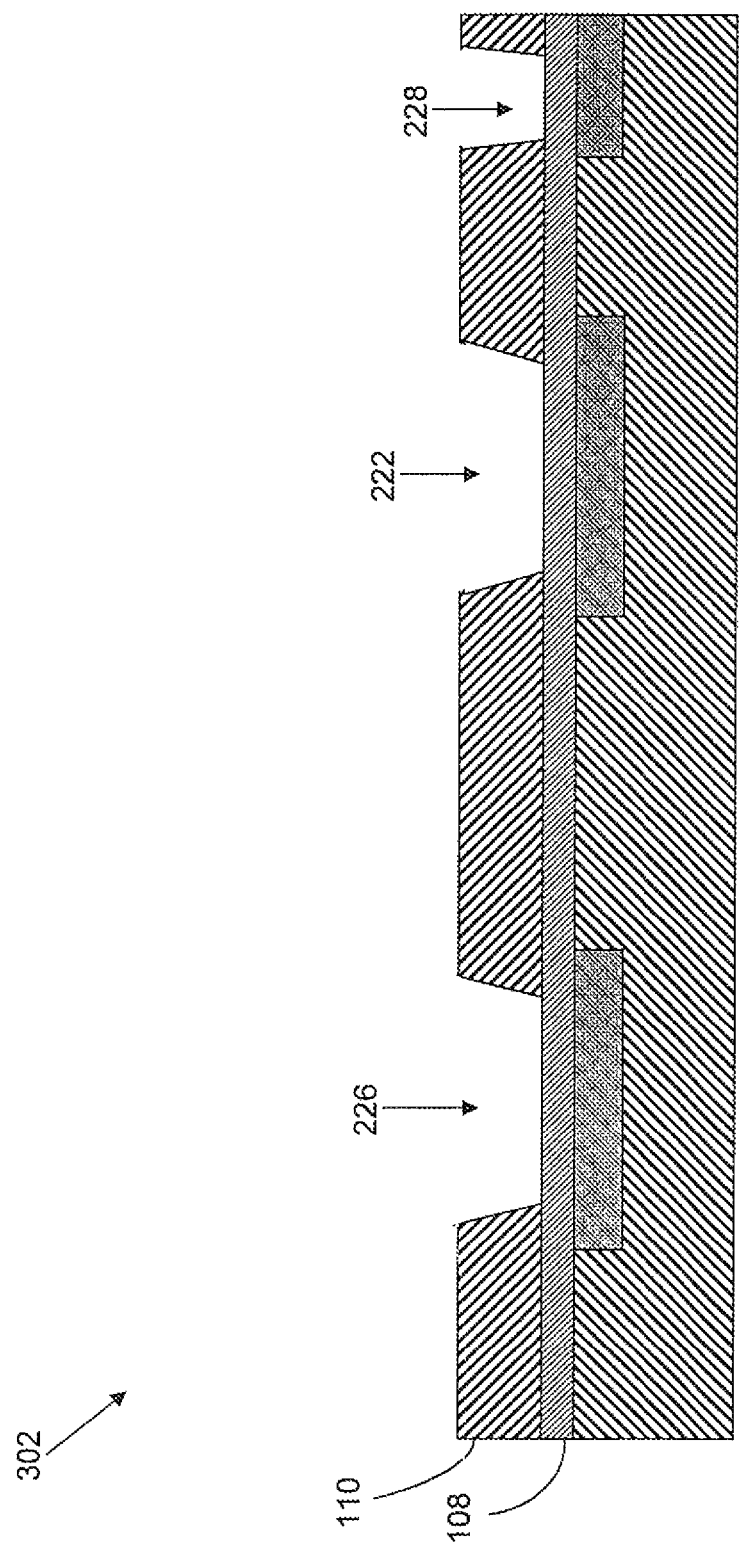

Referring to FIG. 11, a cross sectional view of one alternative embodiment of another process in the forming of a biosensor capacitor 302 in accordance with this invention is shown. As applied to FIG. 3, FIG. 11 shows etching through the isolation layer 110 and exposing the passivation layer 108 forming a bond pad via 226, a counter electrode via 228, and a probe DNA electrode via 222.

Figure 12:
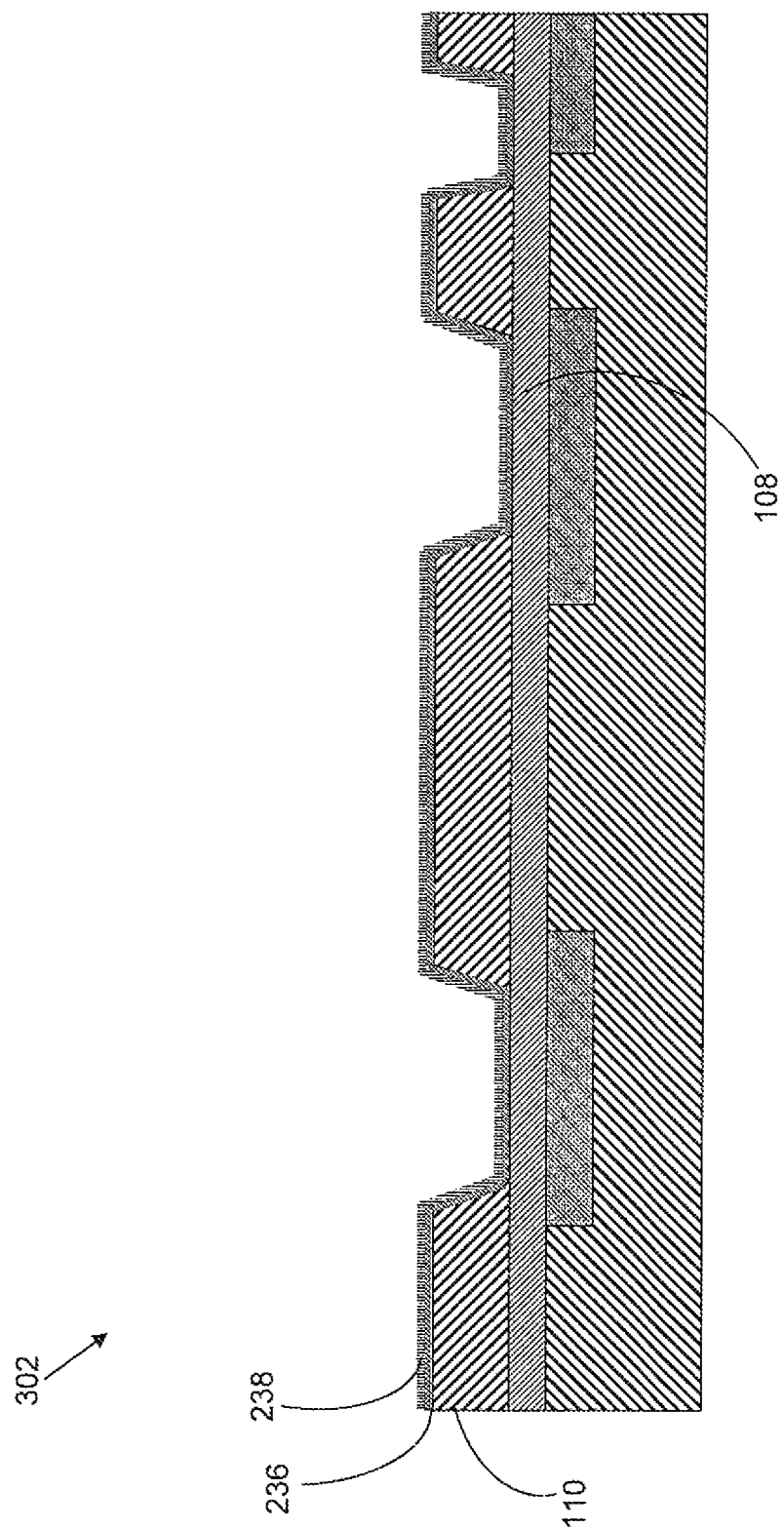
Figure 13:
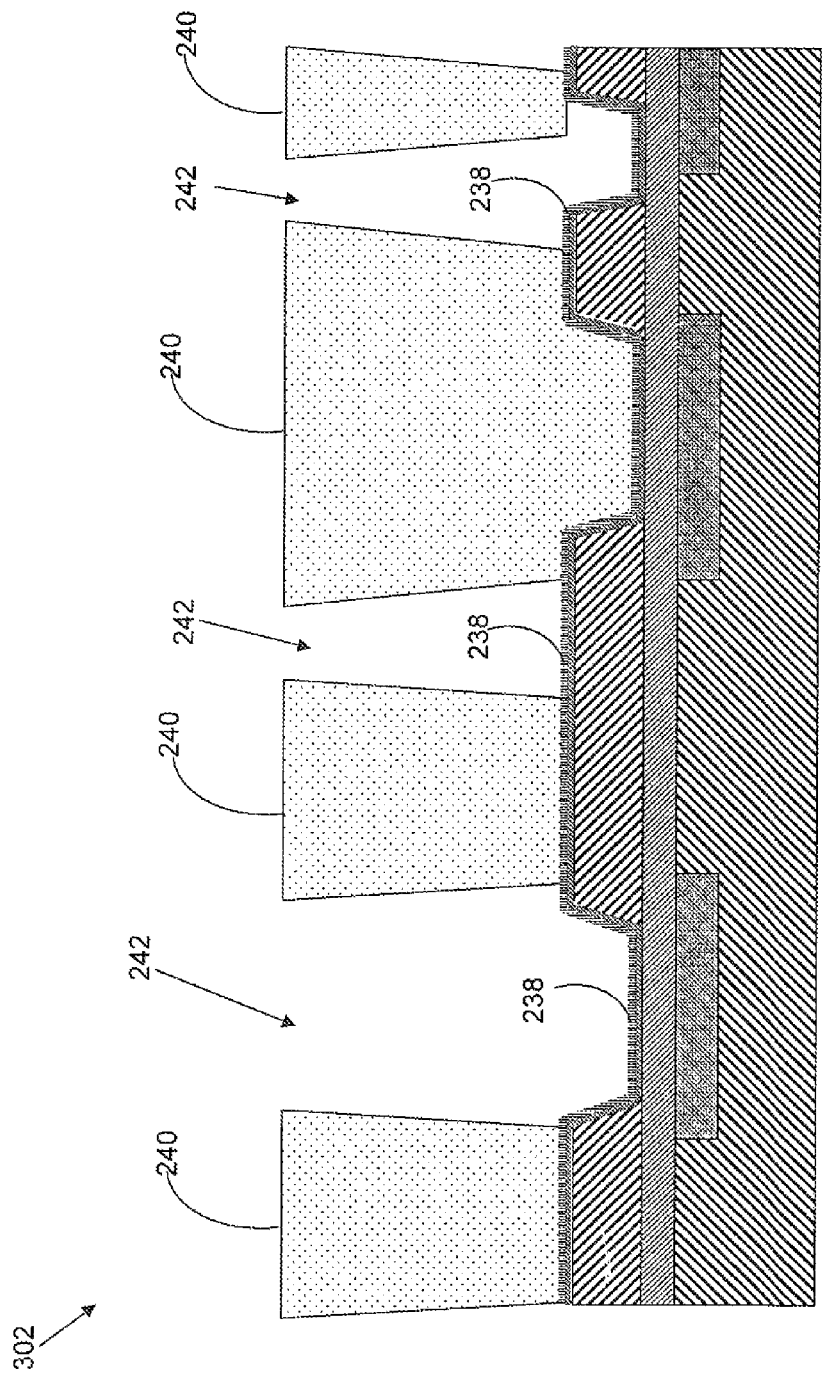
Figure 14:
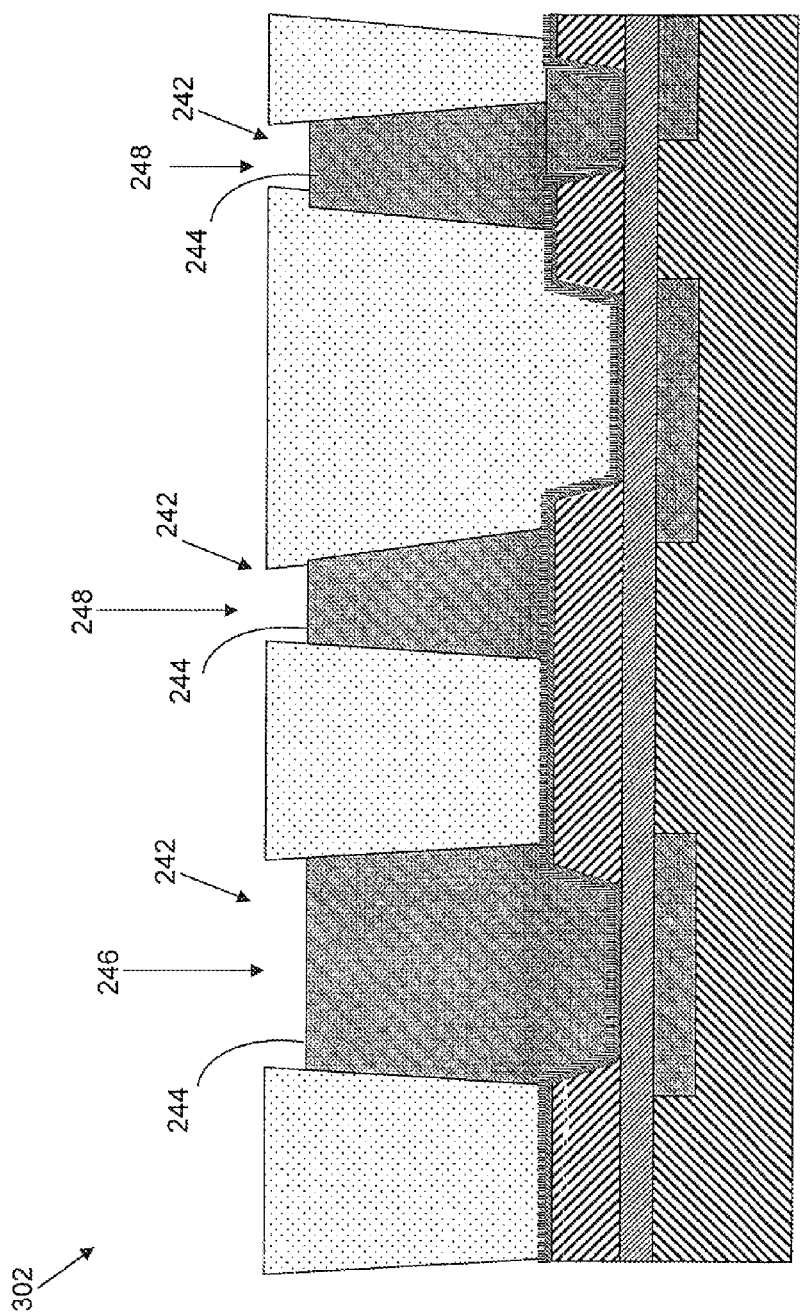
Figure 15:
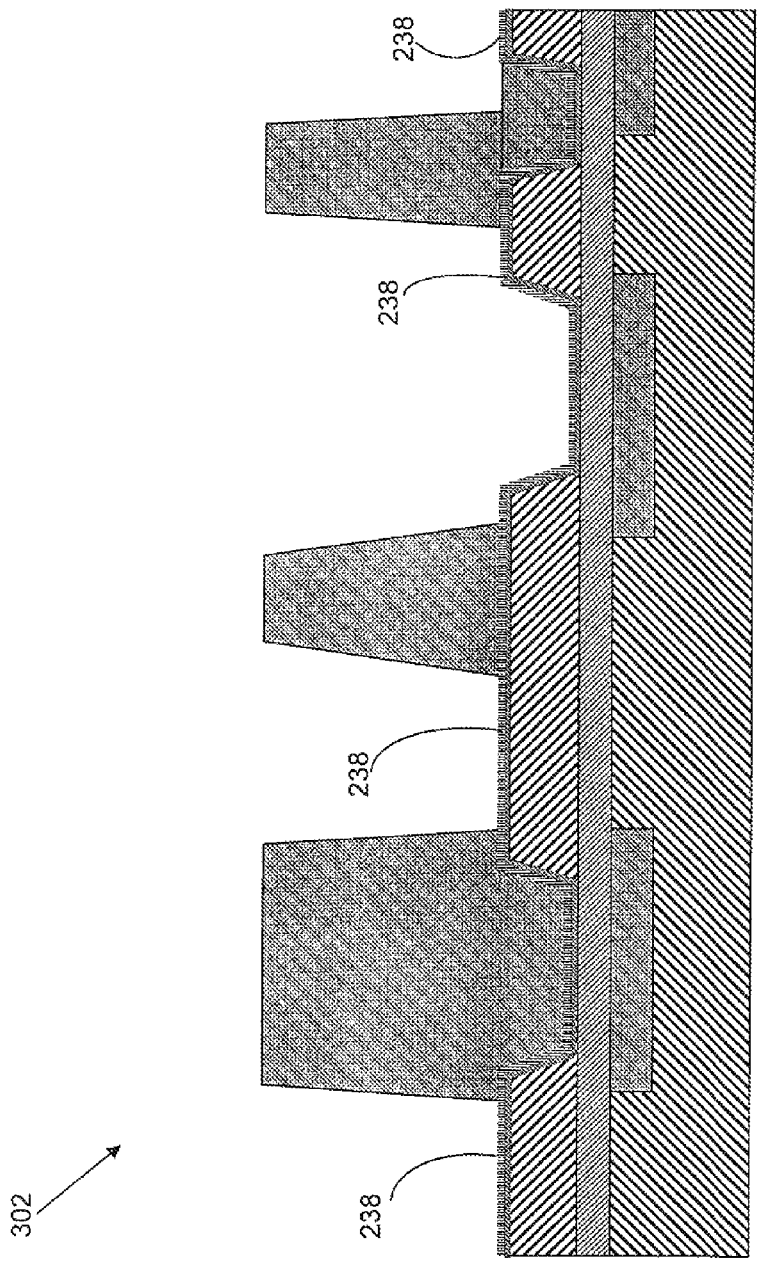
Figure 16:
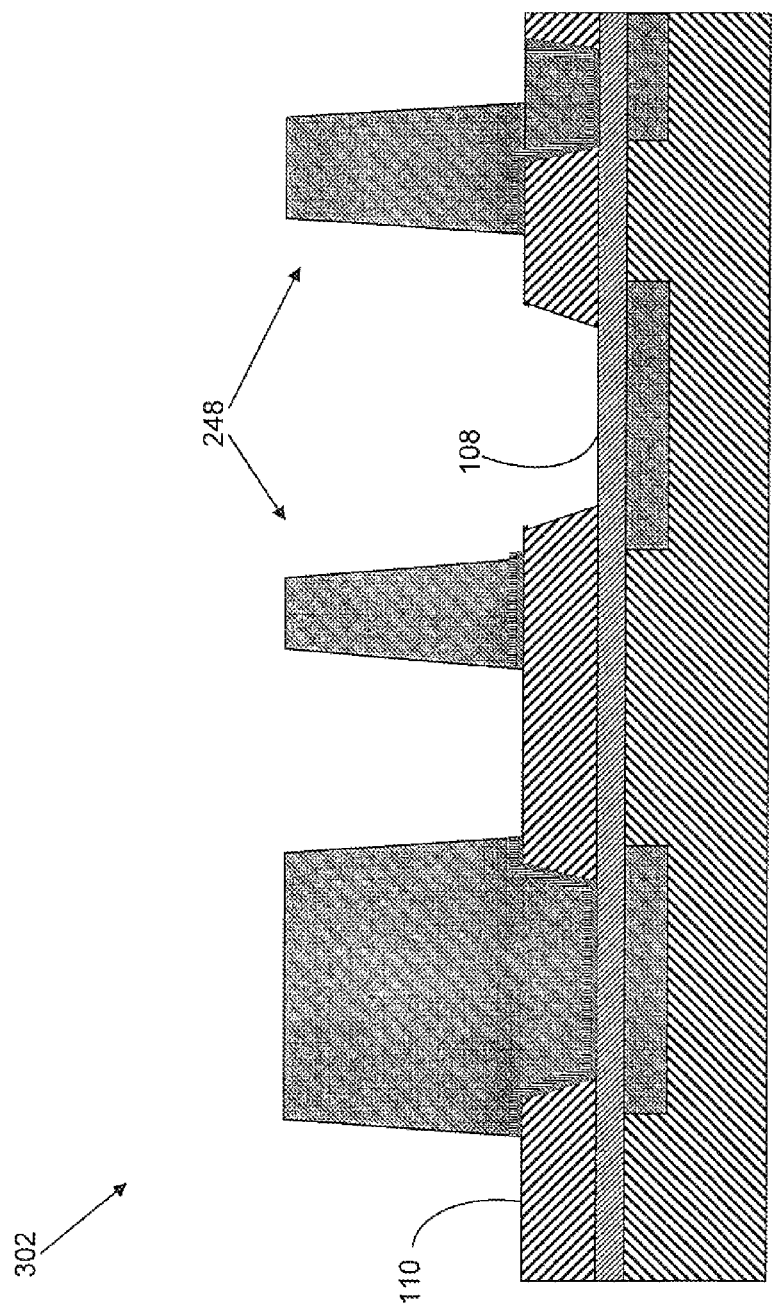
Figure 17:
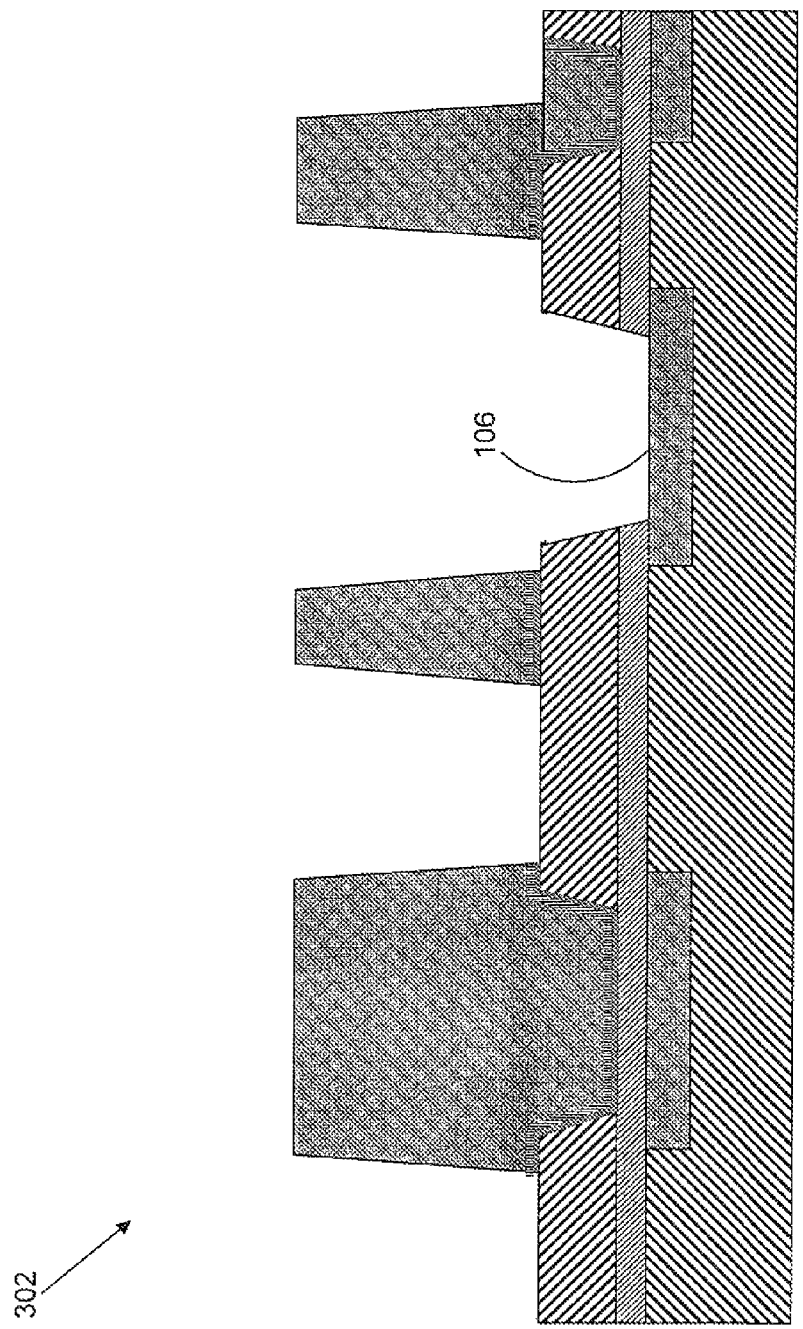
Figure 18:
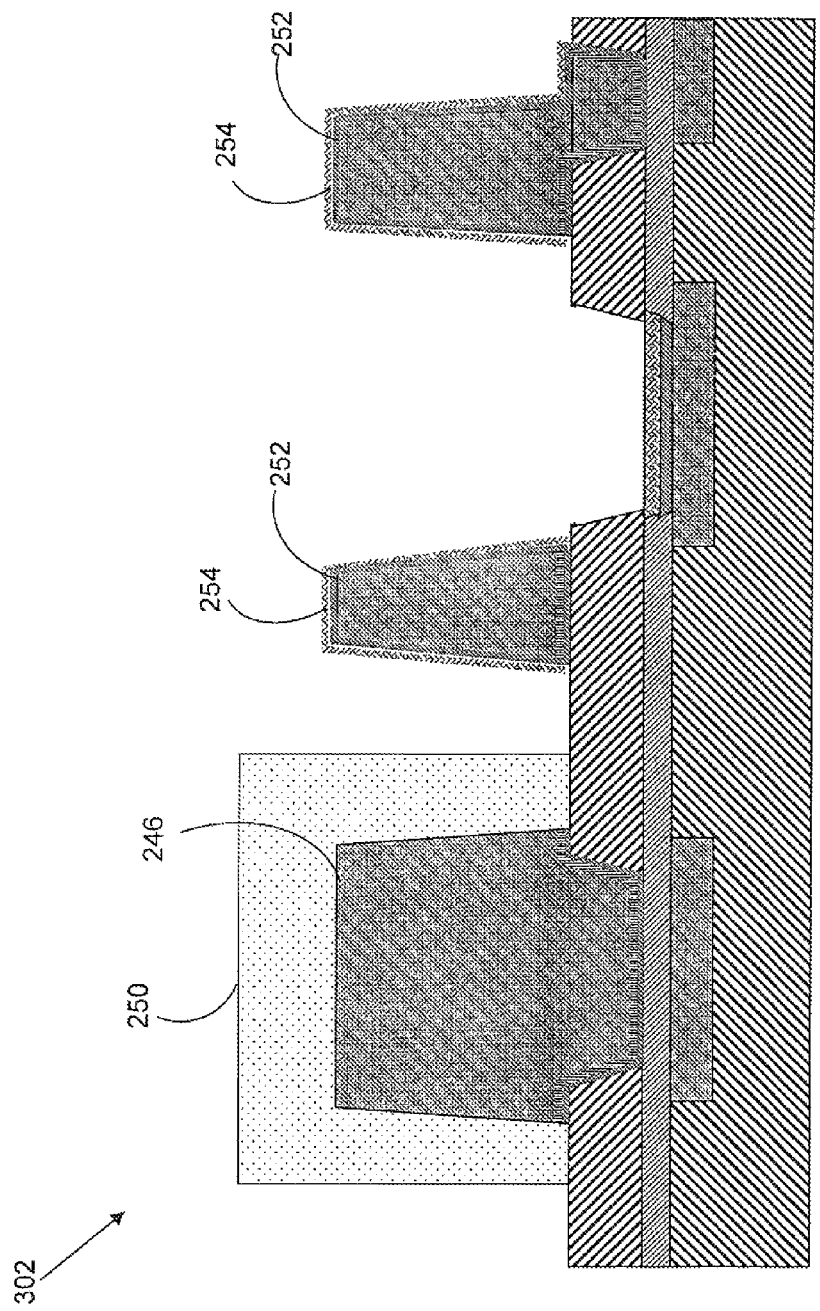
Figure 19:
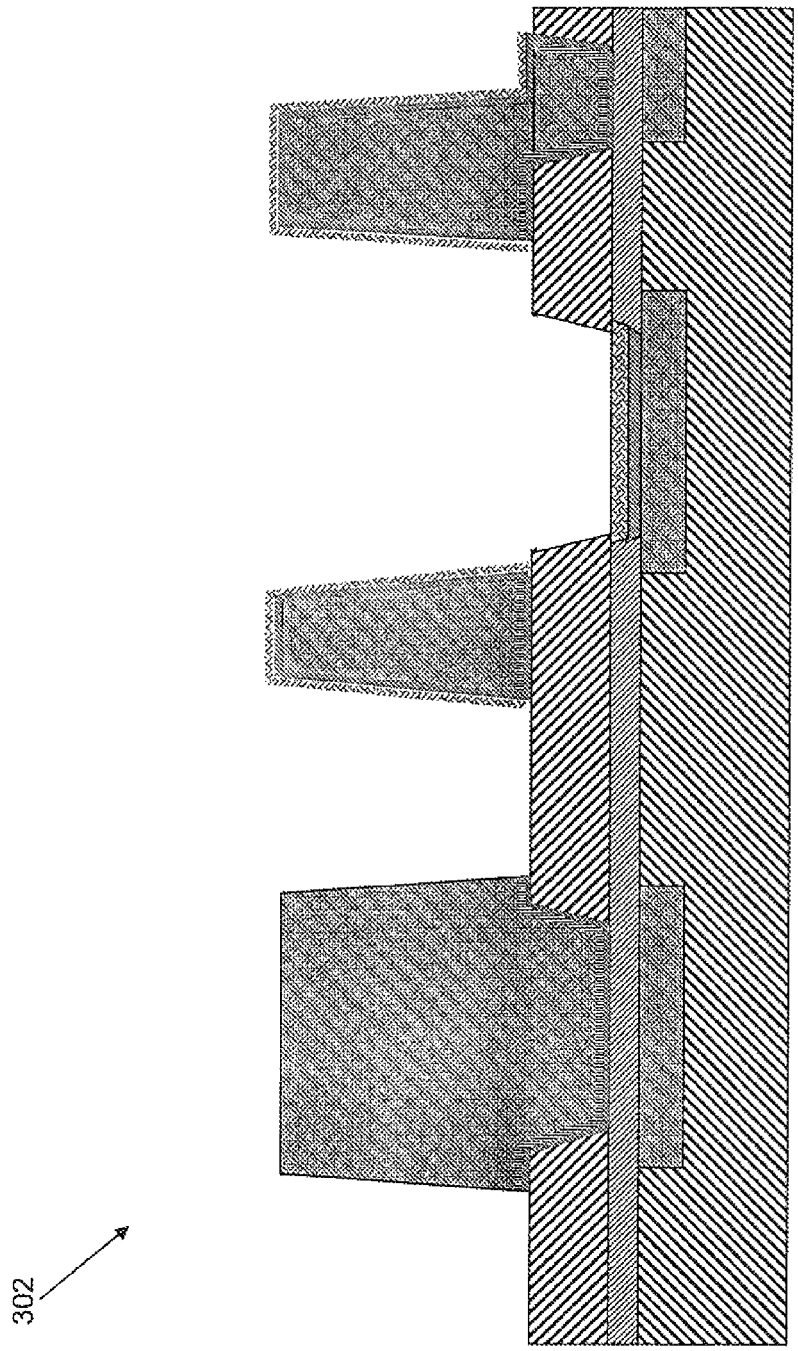

Referring to FIG. 12-19, a cross sectional view of one alternative embodiment of other steps in forming of a biosensor capacitor 302 in accordance with this invention is shown. FIG. 12 shows an adhesion layer 236 deposited (e.g. using sputter deposition) over the isolation layer 110 and the exposed passivation layer 108. Adhesion layer 236 may include, for example, titanium, titanium tungsten, titanium nitride, tantalum, and tantalum nitride. FIG. 12 shows a seed layer 238 deposited (e.g. with sputter deposition) over the adhesion layer 236. Seed layer 238 may include, for example, copper, nickel, and chromium. FIG. 13 shows a first resist pattern 240 applied to portions of the seed layer 238 including a plurality of resist openings 242 exposing the seed layer 238. FIG. 14 shows a copper layer 244 deposited in the plurality of resist openings 242 forming a copper pillar bond pad 246 and two copper pillar counter electrodes 248. Pillars may provide larger surface areas for better sensitivity. FIG. 15 shows the first resist pattern 240 (FIG. 13) stripped to expose areas of seed layer 238. FIG. 16 shows the exposed seed layer 238 (FIG. 15) and adhesion layer 236 (FIG. 15) removed (e.g. by a wet etch) exposing portions of the isolation layer 110 and a portion of the passivation layer 108 between the copper pillar counter electrodes 248. FIG. 17 shows the exposed passivation layer 108 (FIG. 16) etched to expose the first metal layer 106. FIG. 18 shows the application of a second resist pattern 250 to the copper pillar bond pad 246 followed by deposition of a second diffusion barrier 252 over the copper pillar counter electrodes 248 and exposed first metal layer 106 and a deposition of a third metal layer 254 over the second diffusion barrier 252. Second diffusion barrier 252 may include, for example, a refractory metal including cobalt tungsten phosphide ("CoWP"), tantalum ("Ta"), tantalum nitride ("TaN"), tungsten ("W"), and molybdenum ("Mo") and alloys of the refractory metal. Third metal layer 254 may include, for example, gold ("Au"), platinum ("Pt"), palladium ("Pd"), nickel ("Ni"), and chromium ("Cr") and alloys, for example, platinum palladium ("PtPd") and nickel chromium ("NiCr"). FIG. 19 shows the second resist pattern 244 (FIG. 18) stripped.

Figure 20:
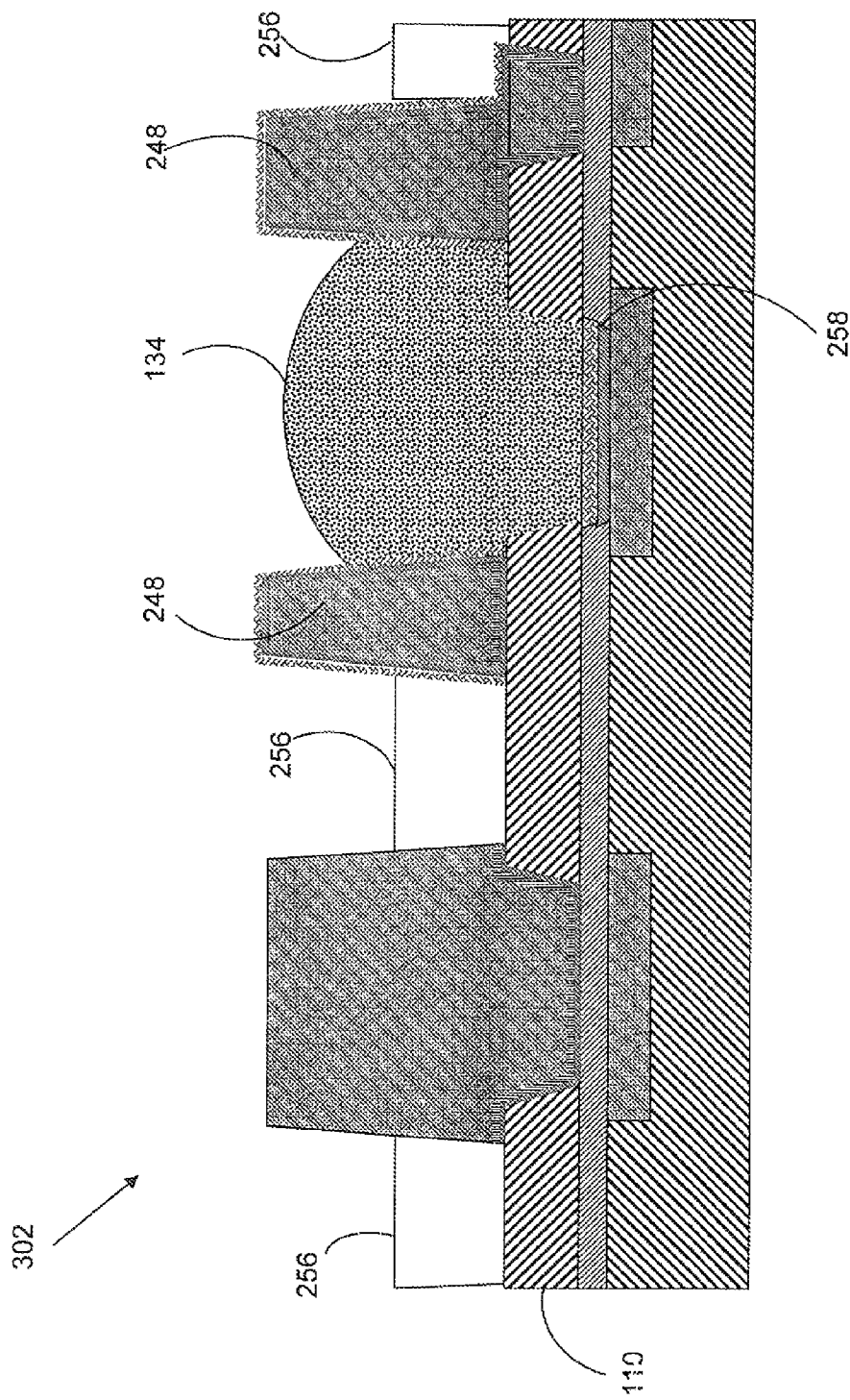

Referring to FIG. 20, a cross-section view of one alternative embodiment of another process in the forming of biosensor capacitor 302 in accordance with this invention is shown. A second protective layer 256 may be deposited over the isolation layer 110. Second protective layer 130 may include, for example, polyimide and other suitable polymer dielectrics. Electrolyte sample 134 is shown deployed above probe DNA electrode 258 and between counter electrodes 248.

Figure 21:
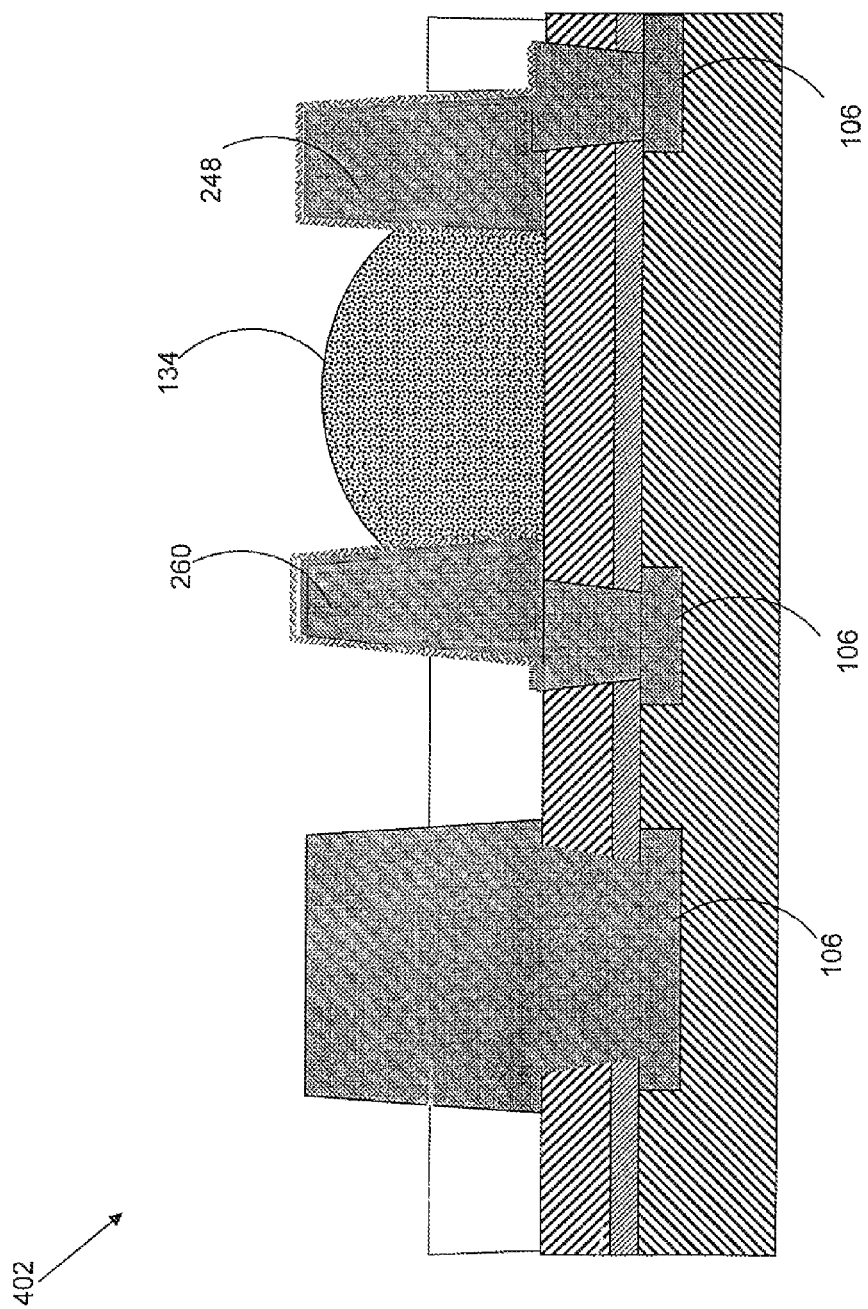
Figure 22:
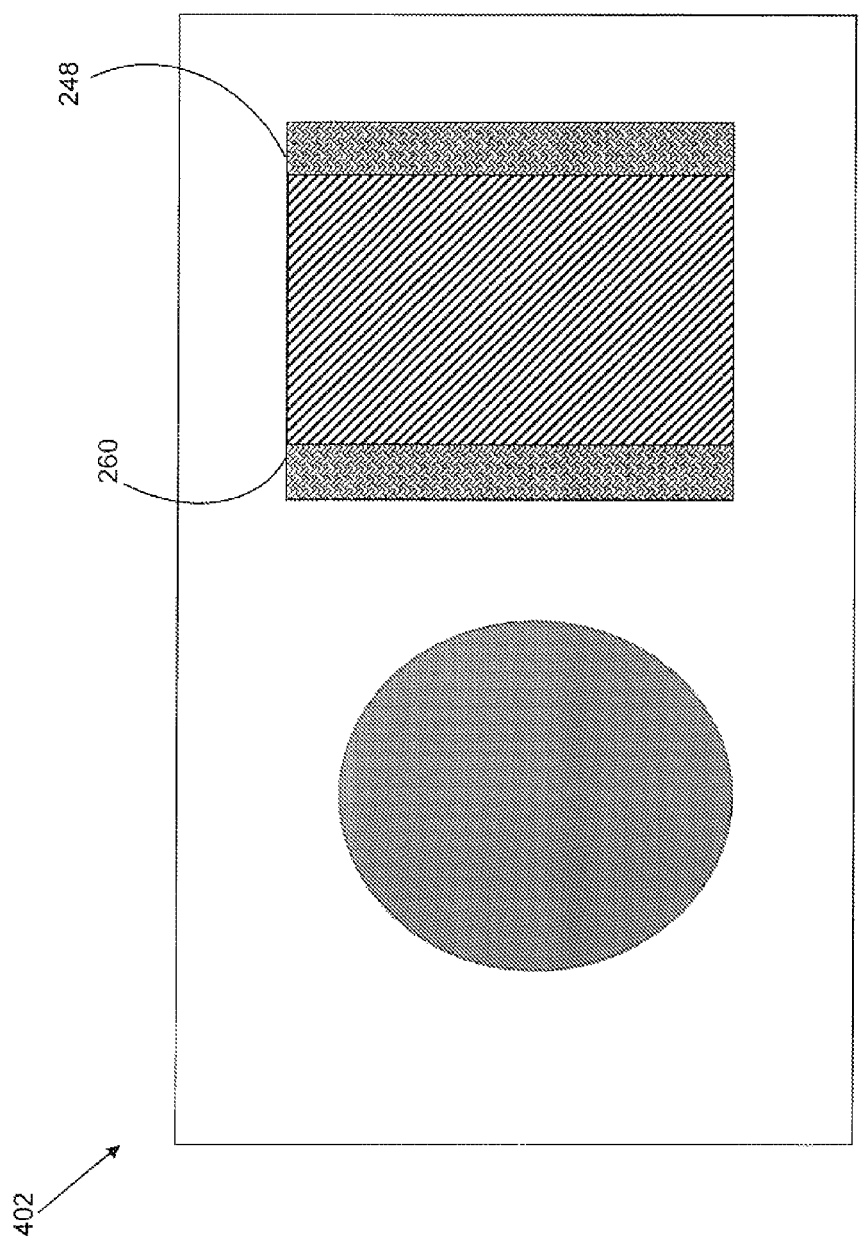

Referring to FIGS. 21 and 22, a cross-section view and top down view respectively of one alternative embodiment of a biosensor capacitor 402 in accordance with this invention is shown. In FIGS. 21 and 22, biosensor capacitor 402 includes the copper pillar counter electrode 248 and a copper pillar probe DNA electrode 260 connecting with first metal layer 106. A via is not formed for an electrode between the copper pillar counter electrode 248 and the copper pillar probe DNA electrode 260. In this embodiment, the copper pillar counter electrode 248 and the copper pillar probe DNA electrode 260 are structurally identical. A person skilled in the art will readily recognize that applying a charge to one of the copper pillar counter electrodes 248 and the copper pillar probe DNA electrode 260 allows that structure to function as the copper pillar probe DNA electrode 260. In other words, the copper pillar counter electrode 248 and the copper pillar probe DNA electrode 260 as illustrated would be switched depending upon which of the two electrodes received a charge. A person skilled in the art will readily recognize variations in the steps described referring to FIGS. 11-19 to form biosensor capacitor 402. Forming biosensor capacitor 402 may require less processing steps than forming biosensor 102 (FIG. 8), 202 (FIG. 9), or 302 (FIG. 20). Electrolyte sample 134 (FIG. 21) is shown deployed inside the copper pillar counter electrode 248 and the copper pillar probe DNA electrode 260.

Figure 23:
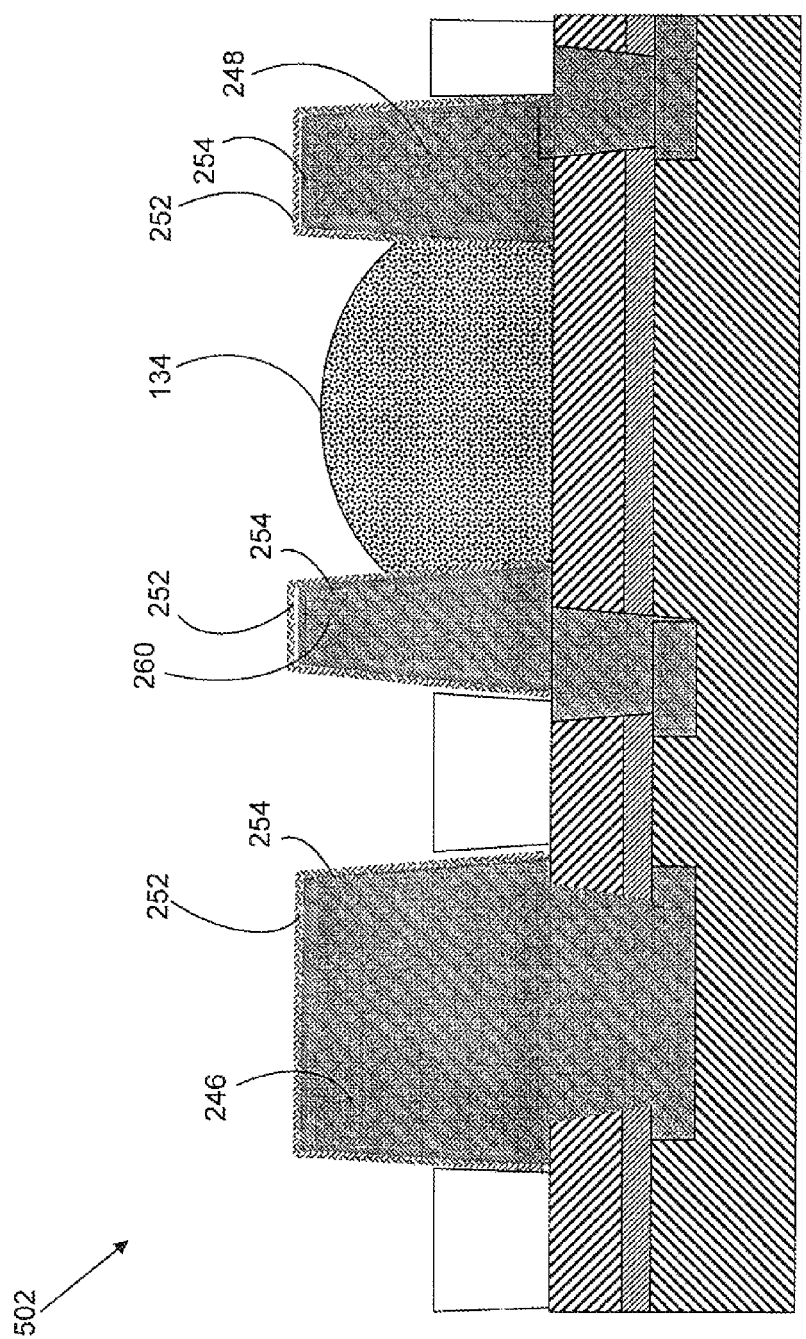

Referring to FIG. 23, a cross-section view of one alternative embodiment of a biosensor capacitor 502 in accordance with this invention is shown. In FIG. 23, biosensor capacitor 502 is similar to biosensor capacitor 402 with the exception of the second diffusion barrier 252 and third metal layer 254 are also deposited on copper pillar bond pad 246 by not applying a second resist pattern 250 to copper pillar bond pad 246 as shown in FIG. 18. Forming biosensor capacitor 502 may require less processing steps than forming biosensor 402 (FIG. 21). Electrolyte sample 134 is shown deployed inside the copper pillar counter electrode 248 and the copper pillar probe DNA electrode 260.

Referring to FIG. 24, a cross-section view of the embodiment of biosensor capacitor 102 (FIG. 8) connected with a plurality of field effect transistors (FET) 372 in accordance with this invention is shown. A person skilled in the art will readily recognize that biosensor capacitor 202 (FIG. 9), 302 (FIG. 20), 402 (FIG. 22), and 502 (FIG. 23) may be connected with the plurality of FETs 372 in a similar manner. The first metal layer 106 of biosensor capacitor 102 may connect with a plurality of vias 364 that may be formed in the dielectric layer(s) 104 of the biosensor capacitor 102 in a known manner. Plurality of vias 364 may include, for example, tungsten, copper, or other suitable material. A person skilled in the art will readily recognize that any number of layers of dielectric layer 104 may be formed. The plurality of vias 364 may connect with a plurality of wires 366 formed in the dielectric layer 104 in a known manner. Plurality of wires 366 may include, for example, copper, aluminum, or other suitable material. The plurality of vias 364 may connect with a plurality of gates 368 formed in the dielectric layer(s) 104 in a known manner. Dielectric layer 104 is deposited above a substrate 370 in a known manner. Plurality of field effect transistors FET 372 are formed between a plurality of shallow trench isolations 372 in the substrate 370 in a known manner. The plurality of vias 364 may connect with the plurality of FET 372. As understood other structures have been omitted for clarity. The omitted structures may include any conventional interconnect components, passive devices, etc., and additional transistors as employed to make SRAMs, etc.

Substrate 370 may be comprised of but not limited to silicon, germanium, silicon germanium, silicon carbide, and those consisting essentially of one or more Group III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and X1+X2+X3+Y1+Y2+Y3+Y4=1 (1 being the total relative mole quantity). Substrate 370 may also be comprised of Group II-VI compound semiconductors having a composition $Zn_{A1}Cd_{A2}Se_{B1}Te_{B2}$, where A1, A2, B1, and B2 are relative proportions each greater than or equal to zero and A1+A2+B1+B2=1 (1 being a total mole quantity). The processes to provide substrate 104, as illustrated and described, are well known in the art and thus, no further description is necessary.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A biosensor capacitor, comprising:
   a dielectric layer;
   a first metal layer in the dielectric layer;
   a first diffusion barrier including a refractory metal over the first metal layer;
   a passivation layer over the dielectric layer and the first metal layer;
   an isolation layer over the passivation layer;
   a probe DNA electrode connected to the first metal layer;
   a counter electrode connected to the first metal layer wherein the counter electrode forms an enclosure around the probe DNA electrode; and
   a bond pad connected to the first metal layer.

2. The biosensor capacitor of claim 1, wherein the probe DNA electrode includes a second metal layer and the counter electrode and the bond pad include aluminum, and wherein the second metal layer comprises one of gold, platinum, palladium, nickel, chromium, platinum palladium alloy, and nickel chromium alloy.

3. The biosensor capacitor of claim 1, wherein the probe DNA electrode and the counter electrode include a second metal layer and the bond pad includes aluminum, and wherein the second metal layer comprises one of gold, platinum, palladium, nickel, chromium, platinum palladium alloy, and nickel chromium alloy.

4. The biosensor capacitor of claim 1, wherein the probe DNA electrode includes a second metal layer and the counter electrode and the bond pad include copper, and wherein the second metal layer comprises one of gold, platinum, palladium, nickel, chromium, platinum palladium alloy, and nickel chromium alloy.

5. The biosensor capacitor of claim 4, further comprising:
   a second diffusion barrier including a refractory metal over the counter electrode; and
   a third metal layer over the second diffusion barrier, wherein the third metal layer comprises one of gold, platinum, palladium, nickel, chromium, platinum palladium alloy, and nickel chromium alloy.

6. The biosensor capacitor of claim 1, further comprising: a wire bond or solder ball connection to the bond pad.

7. A method, comprising:
   forming a bond pad via, a counter electrode via, and a probe DNA electrode via through an isolation layer and a passivation layer to a first metal layer in a dielectric layer;
   forming a first diffusion barrier in each via over the first metal layer;
   forming a probe DNA electrode by forming a second metal layer over the first diffusion barrier in the probe DNA electrode via;
   forming a counter electrode in the counter electrode via, wherein the counter electrode forms an enclosure around the probe DNA electrode via; and
   forming a bond pad in the bond pad via.

8. The method of claim 7, wherein the first diffusion barrier comprises cobalt-tungsten-phosphide, tantalum, tantalum nitride, molybdenum, and nickel or alloys thereof.

9. The method of claim 7, wherein the second metal layer comprises one of gold, platinum, palladium, nickel, chromium, platinum palladium alloy, and nickel chromium alloy and the counter electrode and the bond pad include aluminum.

10. The method of claim 7, wherein the second metal layer comprises one of gold, platinum, palladium, nickel, chromium, platinum palladium alloy, and nickel chromium alloy and the counter electrode includes gold and the bond pad includes aluminum.

11. The method of claim 7, wherein the second metal layer comprises one of gold, platinum, palladium, nickel, chromium, platinum palladium alloy, and nickel chromium alloy and the counter electrode and the bond pad include copper.

12. The method of claim 11, further comprising:
   forming a second diffusion barrier over the counter electrode; and
   forming a third metal layer over the second diffusion barrier, wherein the third metal layer one of gold, platinum, palladium, nickel, chromium, platinum palladium alloy, and nickel chromium alloy.

13. The method of claim 7, further comprising:
   forming a wire bond or a solder ball connection to the bond pad.

14. A biosensor capacitor, comprising:
   a dielectric layer;
   a first metal layer in the dielectric layer;
   a passivation layer over the dielectric layer and the first metal layer;
   an isolation layer over the passivation layer
   a probe DNA electrode including copper connected to the first metal layer;
   a counter electrode including copper connected to the first metal layer;
   a first diffusion barrier including a refractory metal over the counter electrode and the probe DNA electrode;
   a second metal layer over the first diffusion barrier; and
   a bond pad including copper connected to the first metal layer.

15. The biosensor capacitor of claim 14, wherein the first diffusion barrier comprises cobalt-tungsten-phosphide, tantalum, tantalum nitride, molybdenum, and nickel or alloys thereof.

16. The biosensor capacitor of claim 14, further comprising:
   a diffusion barrier including a refractory metal over the counter electrode, the probe DNA electrode, and the bond pad; and
   a third metal layer over the diffusion barrier.

17. The biosensor capacitor of claim 16, wherein the diffusion barrier comprises cobalttungsten-phosphide, tantalum, tantalum nitride, molybdenum, and nickel or alloys thereof.

18. The biosensor capacitor of claim 14, further comprising:
   a wire bond or solder ball connection to the bond pad.

* * * * *